United States Patent [19]

Schottenberger et al.

[11] Patent Number: 5,521,265

[45] Date of Patent: May 28, 1996

[54] METALLOCENES AND THEIR USE FOR OLEFIN POLYMERIZATION

[75] Inventors: Herwig Schottenberger, Salzburg; Michael Buchmeiser, Rohrbach, both of Austria; Olaf Elsner, Gütersloh, Germany; Eberhard Ernst, Katsdorf, Austria; Jens Reussner, Traun, Austria; Wolfgang Neissl, Lichtenberg, Austria; Herbert Angleitner, St. Johann am Walde, Austria

[73] Assignee: PCD Polymere Gesellschaft m.b.H., Linz, Austria

[21] Appl. No.: 408,498

[22] Filed: Mar. 22, 1995

[30] Foreign Application Priority Data

Mar. 22, 1994 [AT] Austria ................................ 594/94

[51] Int. Cl.⁶ ................................................ C08F 4/646
[52] U.S. Cl. .......................... 526/115; 526/117; 526/351; 526/352; 526/348; 526/309; 556/28; 502/113
[58] Field of Search ........................ 556/28; 526/115, 526/117; 502/113

[56] References Cited

U.S. PATENT DOCUMENTS

| | | | |
|---|---|---|---|
| 5,008,302 | 4/1991 | Hüsler et al. | 522/14 |
| 5,096,867 | 3/1992 | Canich | 502/103 |
| 5,106,722 | 4/1992 | Hüsler et al. | 430/325 |
| 5,145,819 | 9/1992 | Winter et al. | 502/117 |
| 5,268,495 | 12/1993 | Riepl et al. | 556/11 |

FOREIGN PATENT DOCUMENTS

| | | |
|---|---|---|
| 1317441 | 5/1993 | Canada . |
| 1319784 | 6/1993 | Canada . |
| 0128046B1 | 12/1984 | European Pat. Off. . |
| 0226675A1 | 7/1987 | European Pat. Off. . |
| 0302424B1 | 2/1989 | European Pat. Off. . |
| 0316155A3 | 5/1989 | European Pat. Off. . |
| 0318894A2 | 6/1989 | European Pat. Off. . |
| 0336128B1 | 10/1989 | European Pat. Off. . |
| 0412416B1 | 2/1991 | European Pat. Off. . |
| 0416566A2 | 3/1991 | European Pat. Off. . |
| 0459264A3 | 12/1991 | European Pat. Off. . |
| 0485823A1 | 5/1992 | European Pat. Off. . |
| 0576970A1 | 1/1994 | European Pat. Off. . |
| 0582195A1 | 2/1994 | European Pat. Off. . |
| 0582194A1 | 2/1994 | European Pat. Off. . |
| 4039451A1 | 6/1992 | Germany . |
| 4211086A1 | 10/1993 | Germany . |

OTHER PUBLICATIONS

Chem Abstr 117:48844 [Broussier et al. (1992) J Organomet Chem 427(2), 231–44].
Chem Abstr. 119:226147 [Oelkers et al. (1993) Organometallics 12(9), 3396–7].
R. L. Halterman, (1992) Chem. Rev. 92, 965, 983–986.
Kaminsky, *Polypropylene '93*, Zurich, Switzerland (1993).
Spaleck et al., *Angew. Chem.*, 104(10), 1373–1376 (1992).
*Chemical Abstracts*, 120:21833s (1994).
*Chemical Abstracts*, 121:84250j (1994).
*Chemical Abstracts*, 120:27145c (1994).
Spaleck et al., *MetCon '93 Houston*, 189–199 (1993).

*Primary Examiner*—Mark Nagumo
*Attorney, Agent, or Firm*—Wenderoth, Lind & Ponack

[57] ABSTRACT

Metallocenes of the formula

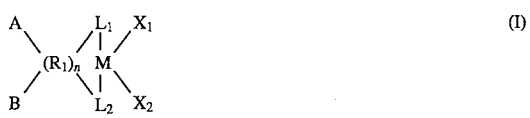

where M is a metal selected from the group consisting of Ti, Zr, Hf, V, Nb, Ta or an element selected from the group of the lanthanides, $X_1$ and $X_2$ are each an alkyl, alkoxy, aryl, aryloxy, alkenyl, arylalkyl, alkylaryl or arylalkenyl group, hydrogen or halogen and $L_1$ and $L_2$ are each a hydrocarbon which can form a sandwich structure with M, where at least $L_1$ or $L_2$ is substituted by or condensed with a ferrocene or ruthenocene radical. $R_1$ is C, Si, Ge or Sn or the whole bridge $A(R_1)_n B$ is a biphenylene radical which is unsubstituted or substituted by A and/or B, A and B have the meanings of $X_1$ and $X_2$, n is an integer from 0 to 4.

5 Claims, No Drawings

METALLOCENES AND THEIR USE FOR OLEFIN POLYMERIZATION

The invention relates to new metallocenes and their use as catalysts in olefin polymerization.

Metallocenes of the metals of the transition group IV of the Periodic Table are highly active catalysts for the polymerization of olefins. The resulting polyolefins possess new property combinations and broaden the product spectrum of the polyolefins prepared hitherto using known conventional Ziegler-Natta catalysts.

It is known that catalysts based on unbridged, substituted and unsubstituted biscyclopentadienyl metallocenes in combination with aluminoxanes as cocatalyst can be used for the preparation of polyethylene and ethylene/α-olefin copolymers (EXXON EP 128046).

Furthermore, it is known that stereoregular polyolefins can be prepared using bridged, chiral metallocenes. For bridging of the ligand systems, use is made mainly of dimethylsilylene groups (CHISSO EP 316155), ethylene groups (Brintzinger et al., J. Organomet. Chem., 288 (1985) 63–67) and isopropylidene bridges (Mitsui Toatsu EP 459264). Depending on the type of ligand and the substituents, isotactic, syndiotactic, hemiisotactic, iso-block-type and atactic homopolymers and copolymers having aliphatic or cyclic structures can be prepared. The ligands preferably used are substituted and unsubstituted cyclopentadienyl units (CHISSO 316155), substituted and unsubstituted indenyl units (Hoechst CA-A 1,317,411, CA-A 1,319,784, U.S. Pat. No. 5,145,819) and also substituted and unsubstituted cyclopentadienyl units in combination with unsubstituted fluorenyl groups (Mitsui Toatsu EP 412416). It is likewise known that bridged metallocenes having one cyclopentadienyl system and one heteroatom ligand ("constrained geometry catalyst") can also be used for the polymerization of olefins (EXXON U.S. Pat No. 5,096,867). Of these various types of metallocene, the bridged, chiral, substituted bisindenyl systems have achieved particular importance. It was thus able to be demonstrated that the type of substituents and the position of the substituents on the ligand of the metallocene exercises a considerable influence on the reactivity of the catalyst system and the stereoregular build-up of the polyolefins obtained. Two substitution possibilities in particular have proven to be advantageous. The first possibility is based on a substitution of the indenyl ring in the 2, 4 and/or 6 position (Hoechst EP 485823; Angew. Chem., 10 (1992) 1373; Spaleck et al., MetCon '93 Houston), the second possibility describes the fusion of the benzene ring of the indenyl ligand with higher condensed aromatic hydrocarbons (Kaminsky, Polypropylene '93 Zurich). Both types of catalyst can be used for the preparation of isotactic polypropylenes and ethylene/alpha-olefin copolymers.

It is thus an object of the invention to find further structural variants of metallocenes as catalysts for the polymerization of olefins. It has now surprisingly been found that ferrocene-substituted or ruthenocene-substituted metallocene systems are suitable catalysts for the preparation of polyolefins.

The present invention accordingly provides metallocenes of the formula I

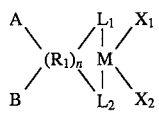

where

M is a metal selected from the group consisting of Ti, Zr, Hf, V, Nb, Ta or an element selected from the group of the lanthanides, $X_1$ and $X_2$ are identical or different and are each a $C_1$–$C_{10}$-alkyl group, a $C_1$–$C_{10}$-alkoxy group, a $C_6$–$C_{10}$-aryl group, a $C_6$–$C_{10}$-aryloxy group, a $C_2$–$C_{10}$-alkenyl group, a $C_7$–$C_{20}$-arylalkyl group, a $C_7$–$C_{20}$-alkylaryl group, a $C_8$–$C_{20}$-arylalkenyl group, hydrogen or a halogen atom, $L_1$ and $L_2$ a) are identical or different and are each an unsubstituted, monosubstituted or polysubstituted monocyclic or polycyclic hydrocarbon radical having at least one cyclopentadienyl unit, which can form a sandwich structure with M, where $L_1$ and/or $L_2$ is substituted by and/or condensed with one or more substituted or unsubstituted ferrocene or ruthenocene radicals, where the substituents can have the same meanings as $X_1$ and $X_2$ or are a ferrocene or ruthenocene radical, or b) $L_1$ is an unsubstituted, monosubstituted or polysubstituted monocyclic or polycyclic hydrocarbon radical having at least one cyclopentadienyl unit, which can form a sandwich structure with M and which is substituted by and/or condensed with one or more substituted or unsubstituted ferrocene or ruthenocene radicals, where the substituents have the same meanings as $X_1$ and $X_2$ or are a ferrocene or ruthenocene radical and $L_2$ is an amido, phosphido or arsenido radical of the formula

where D is nitrogen, phosphorus or arsenic and E has the meaning of $X_1$ and $X_2$, $R_1$ is carbon, silicon, germanium or tin, or the entire bridge $A(R_1)_n B$ can be a biphenylene radical which is unsubstituted or substituted by A and/or B, A and B have the meanings of $X_1$ and $X_2$ and n is an integer from 0 to 4, where in the case n=0 the free valencies of $L_1$ and $L_2$ are substituted by a radical $X_1$ or $X_2$ with the proviso that in the case of $L_2$ being an amido, phosphido or arsenido radical, n is not equal to zero.

Particularly preferred radicals $L_1$ and $L_2$ are ferroceno[2,3]inden-1-yl, ferroceno[2,3]cyclopentadien-1-yl, 4-ferrocenylferroceno[2,3]cyclopentadien-1-yl, or 9-ferrocenylfluorenyl, or, as radicals $L_2$, additionally cyclopentadienyl, tetramethylcyclopentadienyl, inden-1-yl, 2-methylinden-1-yl, fluorenyl.

According to the invention, the following metallocenes are particularly preferred: bis (ferroceno[2,3]inden-1-yl)dimethylsilylenezirconium dichloride, rac-(ferroceno[2,3]inden-1-yl)dimethylsilylene(tetramethylcyclopentadienyl)zirconium dichloride, rac-(ferroceno[2,3]inden-1-yl)dimethylsilylene(cyclopentadienyl)zirconium dichloride, rac-(ferroceno[2,3]inden-1-yl)dimethylsilylene(2-methylinden-1-yl)hafnium dichloride, rac-(ferroceno[2,3]inden-1-yl)dimethylsilylene(fluoren-9-yl)zirconium dichloride, rac-(ferroceno[2,3]inden-1-yl)dimethylsilylene(t-butyl-amido)zirconium dichloride, rac-(4-ferrocenylferroceno[2,3]cyclopentadienyl)dimethylsilylene(tetramethylcyclopentadienyl)zirconium dichloride, bis(4-ferrocenylferroceno[2,3]cyclopentadienyl)dimethylsilylenezirconium dichloride and bis(9-ferrocenylfluorenyl)titanium dichloride.

The invention further provides a process for preparing the metallocenes according to formula I, which is characterized in that a compound of the formula II $$\left[ \begin{array}{c} A \\ | \\ L_1 \!+\! R_1 \!+\!_n L_2 \\ | \\ B \end{array} \right] (M')_2 \quad \text{(II)}$$

is reacted with a compound of the formula III $$M(X')_2 X_1 X_2 \quad \text{(III)}$$

where $L_1$, $L_2$, A, B, $R_1$ or the bridge $A(R_1)_n B$, M, $X_1$, $X_2$ and n have the meanings given above, M' is an alkali metal or an alkaline earth metal and X' is a halogen atom. Particularly preferably, M' is lithium, X' is chlorine.

The metallocenes of the formula I can be prepared, for example, according to the following reaction scheme:

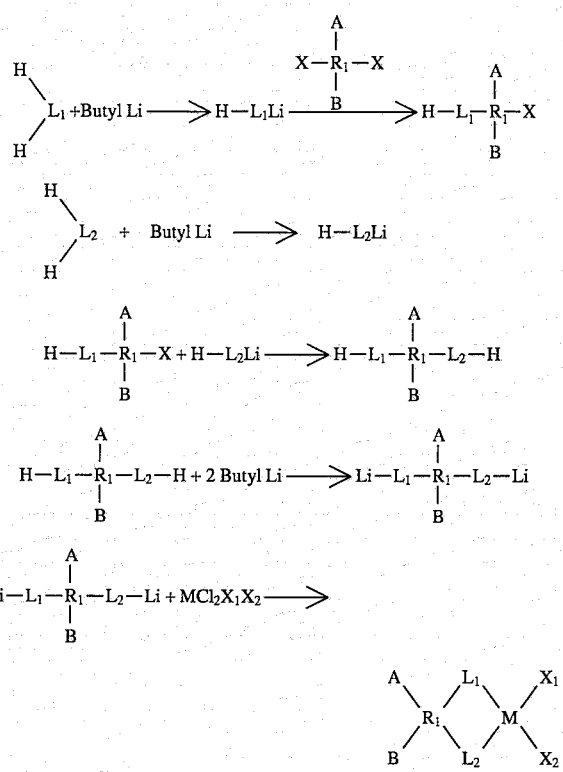

$X=F$; Cl; Br; I $X_1/X_2$; $L_1$ and $L_2$ have the meanings given above.

Examples of processes for preparing the metallocenes are given in the examples.

Examples of ligands $L_1$ or $L_2$ are those selected from the groups shown below:

a) ferroceno[1,2]cyclopenta-1,3-diene or ruthenoceno[1,2]cyclopenta-1,3-diene

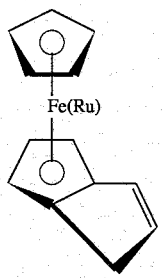

b) ferroceno[2,3]ind-1-ene or ruthenoceno[2,3]ind-1-ene

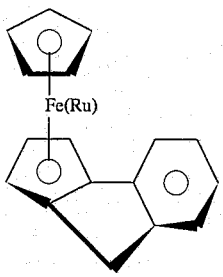

c) 9-ferrocenylfluorene or 9-ruthenocenyl[2,3]fluorene

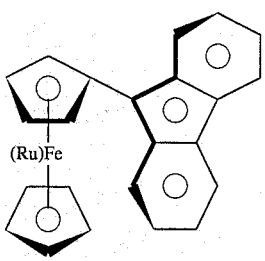

The compounds of these groups can, if desired, be variously substituted, where the substituents have the meanings of $X_1$ and $X_2$ or else are substituted by or fused with ferrocenyl or ruthenocenyl.

In the case of the unsymmetrical metallocenes, the ligands $L_2$ used can be, for example, variously substituted or unsubstituted cyclopentadienyl, indenyl, fluorenyl or amido, phosphido and arsenido compounds, where the substituents of these ligands have the meanings of $X_1$ and $X_2$ or else are substituted by or fused with ferrocenyl or ruthenocenyl.

The invention further provides for the use of the metallocenes of the invention as polymerization catalysts in the polymerization of olefins, and also an olefin polymerization process in which the metallocenes of the invention are used as catalysts.

The olefin polymerization is preferably carried out using a cocatalyst, for example an aluminoxane of the formula IV for the linear type:

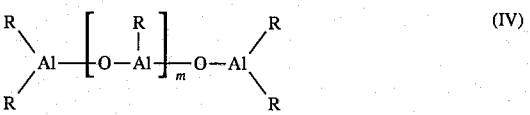 (IV)

and/or the formula V:

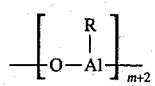 (V)

for the cyclic type, where in the formulae IV and V the radicals can be identical or different and are each a $C_1$–$C_6$-alkyl group, a $C_6$–$C_{10}$-aryl or alkylaryl group and m is an integer of 1–50. Preferably, the radicals are identical and are methyl, isobutyl, phenyl or benzyl, particular preference being given to methyl. The aluminoxane can be prepared in various ways by known methods. One possibility is, for example, the reaction of aluminum alkyls with aluminum sulfate containing water of crystallization (Hoechst EP 302424). In the present invention, commercial MAO (methylaluminoxane, from Witco, FRG) is used.

It is also possible to mix the metallocene of the formula I with an aluminoxane of the formula IV and/or V prior to use in the polymerization reaction. The mixing is preferably carried out in solution. The metallocene is here preferably dissolved in an inert hydrocarbon and subsequently mixed with the aluminoxane solution. Suitable inert hydrocarbons are, for example, aliphatic or aromatic hydrocarbons. Preference is given to using toluene.

The concentration of the aluminoxane in the solution is usually in the range of 5–30% by weight based on the total solution. The metallocene is preferably used in an amount of from $10^{-4}$ to 1 mol per mole of aluminoxane. The mixing time is from about 5 minutes to 24 hours, preferably from 5 to 60 minutes. The mixing is usually carried out at a temperature of from $-10°$ to $+70°$ C., in particular at from $10°$ to $40°$ C. The metallocene can also be applied to a support. Suitable supports are, for example, the inorganic oxides of the metals of the main groups II–IV of the Periodic Table. Preference is given to the oxides of the metals magnesium, calcium, aluminum, silicon, boron and their mixtures. Particular preference is given to, for example, the commercially available aluminum oxides "Alumina Typ C" (Degussa) and silicon oxides of the type "Silica Davison Grade 952–957" or of the type Aerosil (Degussa), and also mixtures of $Al_2O_3$ and $SiO_2$. The polymerization can be carried out in solution, suspension or gas-phase processes, continuously or batchwise at a temperature of from $-10°$ to $+200°$ C., preferably from $+20°$ to $+80°$ C. Olefins of the formula $R^a$—CH=CH—$R^b$ are polymerized or copolymerized. In this formula, $R^a$ and $R^b$ are identical or different and are each a hydrogen atom or an alkyl radical having from 1 to 20 carbon atoms. However, $R^a$ and $R^b$ can also form a ring with the carbon atoms connecting them. For example, olefins such as ethylene, propylene, 1-butene, 1-hexene, 4-methyl-1-pentene, 1-octene, cyclopentene, norbornene or norbornadiene are polymerized or copolymerized. In particular, ethylene, propylene and cyclopentene are polymerized or copolymerized.

As molecular weight regulator, if required, hydrogen is added. The total pressure of the polymerization is 0.5–150 bar. Preference is given to carrying out the polymerization in the pressure range of 1–40 bar.

It has been found to be advantageous to carry out the reaction of the monomers in the presence of the metallocene catalyst system at a molar ratio of aluminum of the oligomeric aluminoxane compound to the transition metal of the metallocene compound of from $10^6$:1 to $10^1$:1, preferably from $10^4$:1 to $10^2$:1.

If the polymerization is carried out as a suspension or solution polymerization, an inert solvent is used. For example, aliphatic or cycloaliphatic hydrocarbons such as pentane, hexane or cyclohexane can be used. It is also possible to use toluene. Polymerization is preferably carried out in the liquid monomer.

In the copolymerization of ethylene with propylene, the polymerization is preferably carried out in liquid propylene or in hexane as suspension medium. In the polymerization in liquid propylene, the ethylene is preferably fed in in such an amount that a partial pressure ratio $p_{c2}/p_{c3}$ of greater than 0.5, in particular greater than 1.0, is established above the liquid phase ($P_{c2}$=partial pressure of the ethylene in the gas phase above the suspension; $P_{c3}$=partial pressure of the propylene in the gas phase above the suspension). In the copolymerization in hexane as suspension medium, an ethylene/propylene gas mixture having a propylene content of from 1 to 50 mol %, preferably from 5 to 30 mol %, is added. The total pressure is kept constant during the polymerization by metering in further amounts.

The duration of the polymerization is generally from about 10 minutes to 6 hours, preferably from 30 minutes to 2 hours.

The catalysts used according to the invention expand the range of polymerization-active metallocenes for preparing polyolefin homopolymers and copolymers. In particular, the metallocenes of the invention produce, in the industrially interesting temperature range between $20°$ and $80°$ C., polymers and copolymers having a broad molecular weight distribution, which are in the range of polyolefins prepared using classical Ziegler-Natta catalysts.

The following examples illustrate the invention. Abbreviations used are:

| | | |
|---|---|---|
| $M_w$ = | weight average molecular weight in g/mol, | |
| $M_n$ = | number average molecular weight in g/mol, | |
| $M_w/M_n$ = | molecular weight distribution, determined by gel permeation chromatography, | |
| MS | mass spectroscopy | |
| $^1$H-NMR | $^1$H nuclear magnetic) resonance spectroscopy) | elucidation of |
| $^{13}$C-NMR | $^{13}$C nuclear magnetic) resonance spectroscopy) | the catalyst structure |
| IR | infrared spectroscopy | |

EXAMPLE I rac-(4-Ferrocenylferroceno[2,3]cyclopentadienyl)dimethylsilylene(tetramethylcyclopentadienyl)zirconium dichloride

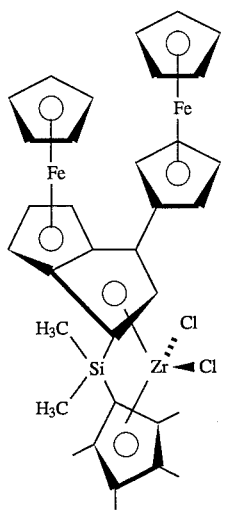

A) 3-Ferrocenylferroceno[1,2]cyclopenta-1,3-diene 1.33 g (3.15 mmol) of 4-ferrocenylferroceno[2,3]cyclopenta-2,4-dien-1-one (T. S. Abram, W. E. Watts, J. Chem. Soc., Perkin I, 1531 (1977) are dissolved in 30 ml of THF and admixed at $0°$ C. with 2.5 ml of lithium triethylborohydride (1.26M in THF; 3.15 mmol). After stirring for 10 minutes at room temperature, the THF is drawn off, the residue is admixed with 0.5 ml of water, 100 ml of diethyl ether and also 1.0 ml of tetrafluoroboric acid diethyl etherate. After the suspension had been treated for 5 minutes with ultrasound, the deep blue suspension is filtered through a Schlenk tube. The residue is washed repeatedly with diethyl ether and dried in vacuo.

The cation is dissolved in 20 ml of THF and admixed at $-50°$ C. with a solution of 250 mg of sodium (10.9 mmol) in 50 ml of ammonia. The reaction solution is warmed to room temperature, poured onto saturated ammonium chloride solution and extracted with diethyl ether. The crude product is, after removal of the diethyl ether, chromatographed over Alox (basic, Merck, activity stage IV). Mobile phase: diethyl ether: n-hexane=50:50, 2% diethylamine.

Yield: 800 mg (corresponds to a yield of 62% of theory)

B) Reaction to give (4-ferrocenylferroceno[2,3]cyclopentadienyl)dimethylsilylene(tetramethylcyclopentadienyl)zirconium dichloride 400 mg of 2-ferrocenylferroceno[3,4]cyclopenta- 1,3-diene (0.94 mmol) are dissolved in 30 ml of THF and admixed at −50° C. with 0.60 ml of n-butyllithium (1.6M in hexane, 0.96 mmol). After 5 minutes, the deep blue solution is admixed with 0.22 ml of tetramethylcyclopentadienyldimethylchlorosilane (1 mmol) (D. Stern, M. Sabat, T. J. Marks, *J. Am. Chem. Soc.* 112 (1.990) 9558). After the solution has been brought to room temperature and again cooled to −50° C., the solution is admixed with 1.2 ml of n-butyllithium (1.6M in hexane, 1.92 mmol) and 380 mg of zirconium tetrachloride·2THF (1.0 mmol). The solution is subsequently refluxed for 1 hour. After removal of the solvent, the residue is washed with n-hexane and subsequently dissolved in 20 ml of diethyl ether. After a Schlenk filtration, the solvent is removed in vacuo. The residue, a brownish powder, rapidly discolors in air, on storage it becomes deep green after some time. All spectra were obtained on the green modification.

IR (KBr): 3400b,vs; 2970w, 2917w; 2856w; 1634b,vs; 1532m; 1457w; 1412w; 1383w; 1258m, 1181w; 1106m, 1046m; 1001w; 803b,s; 589vb,s, 482b,s.

$^1$H-NMR (CDCl$_3$, TMS): dimethylsilylene region: −0.05 ppm(s), 0.07 ppm(s), tetramethyl Cp region: 1.75–1.95 ppm(m); 1.15–1.40 ppm(m); 1.77 ppm(s) 1.90 ppm(s); 1.96 ppm(s); 2.05 ppm(s); 2.18 ppm(s); ferrocene region: 3.70 ppm(s); 3.8–4.5 ppm(m); 4.08 ppm(s).

$^{13}$C-NMR (CDCl$_3$, TMS): −0.17 ppm; 0.22 ppm; 0.86 ppm, 1.50 ppm; 13.67 ppm; 13.76 ppm; 17.95 ppm, 18.72 ppm; 25.50 ppm; 26.22 ppm; 26.33 ppm; 66.8 ppm; 67.9 ppm; 68.6 ppm; 69.1 ppm; 70.5 ppm.

MS (EI, 70 eV): m/e=746.5 (M$^+$·, 51%) 369 (tetramethylcyclopentadienyldimethylsilylenepentalenylzirconium, 61%)

Microprobe: C, Fe, Cl, Zr, Si in a consistent elemental ratio.

EXAMPLE II rac-(Ferroceno[2,3]inden-1-yl)dimethylsilylene(2-methylinden-1-yl)hafnium dichloride 400 mg (1.46 mmol) of ferroceno[2,3]indene (M. Cais, A. Modiano, A. Raveh, *J. Am. Chem. Soc.*, 87, 5607 (1965); T. Lanez, P. L. Pauson, *J. Chem. Soc.* Perkin 1, 2437 (1990)) are dissolved in 30 ml of absolute THF, cooled to −50° C. and admixed with 0.95 ml of n-butyllithium (1.6M in hexane, 1.52 mmol). After 90 minutes, 1.9 ml of dimethyldichlorosilane (15 mmol) are added. After 5 minutes, all the solvent and the excess of dimethyldichlorosilane are drawn off in vacuo. The residue is dissolved in THF and admixed with a solution of 2-methylindenide in 30 ml of THF, prepared from 30 ml of 2-methylindene (C. F. Koelsch, P. R. Johnson, *J. Am. Chem. Soc.*, 65, 567 (1943); with about 35% of hexane, about 1.5 mmol) and 0.95 ml of n-butyllithium in 30 ml of THF at −50° C. The mixture is then stirred for 30 minutes at room temperature. After again cooling to −50° C., 1.9 ml of n-butyllithium (1.6M in hexane, 3.04 mmol) are added. Finally, 490 mg of hafnium tetrachloride (1.5 mmol), dissolved in 30 ml of THF, are added after warming to room temperature and again cooling to −50° C. The reaction mixture is refluxed for 90 minutes. After removal of the solvent, the residue is dissolved in diethyl ether and filtered through a Schlenk tube. A red discoloration of the product is attributable to traces of lithium 2-methylindenide. These can be avoided by removal of the solvent prior to the last deprotonation step. After drawing off the ether in vacuo, about 500 mg of product (50% of theory) remain.

IR (KBr): 3402vb,vs; 2929s; 2858s; 1617b,s; 1463s, 1439m; 1382m; 1267w; 1254m; 1106s; 1067s; 1019s; 965m; 845s; 807s; 753s.

$^1$H-NMR (CDC$_3$, TMS): by means of the ferrocene part, 2 diastereomeric compounds (a, b) can be observed in a ratio of (about) 10:1. Dimethylsilylene region: −0.65 ppm(s); methyl region: 2.00 ppm(s); ferrocene region: 3.71 ppm(s, a); 4.23 ppm ("t", a); 4.04 ppm("t", a); 3.90 ppm(d×d, a); 3.74 ppm (s, b); 4.14 ppm("t", b); 4.54 ppm(d×d, b); 4.58 ppm (d×d, b); indene region: 5.51 ppm(s); aromatic region: 6.97–7.57 ppm(m).

$^{13}$C-NMR (CDCl$_3$, TMS): SiMe$_2$: −7.43 ppm; methyl: 35.6 ppm; 35.8 ppm; ferrocene region: 58.7 ppm; 58.8 ppm; 61.3 ppm, 61.4 ppm; 69.5 ppm; 70.1 ppm quaternary C: 91.8 ppm; 95.0 ppm; 101.1 ppm; 103.4 ppm; 106.1 ppm aromatic region: 119.6 ppm; 120.3 ppm; 122.7 ppm; 123.2 ppm; 123.5 ppm; 123.7 ppm; 124.0 ppm; 124.2 ppm; 124.3 ppm; 124.6 ppm; 124.9 ppm; 125.2 ppm; 125.4 ppm; 126.2 ppm; 126.7 ppm; quaternary C: 137.7 ppm; 141.5 ppm; 149.3 ppm.

MS (EI, 70 eV): m/e=508.5 (M$^+$−200, 36%); 379 (91%); 272 (ferroceno[2,3]inden-1-yl, 22%)

Microprobe: C, Fe, Cl, Si, Hf in a consistent elemental ratio.

EXAMPLE III

Bis(ferroceno[2,3]inden-1-yl)dimethylsilylenezirconium dichloride

A) Bis(ferroceno[2,3]inden-1-yl)dimethylsilane 280 mg of ferroceno[2,3]indene (M. Cais, A. Modiano, A. Raveh, *J. Am. Chem. Soc.*, 87, 5607 (1965)) (1.02 mmol) are dissolved in 30 ml of THF, cooled to −60° C. and admixed with 0.55 ml of n-butyllithium (2M in hexane, 1.1 mmol). The mixture is warmed to room temperature, stirred for a further 15 minutes, again cooled to −60° C. and 0.145 ml of dimethyldichlorosilane (1.12 mmol) is added. After warming to room temperature, the solvent is drawn off. Monitoring for complete and quantitative reaction can be carried out using thin-layer chromatography.

B) Reaction to give bis(ferroceno[2,3]inden-1-yl)dimethylsilylenezirconium dichloride The orange solid is again dissolved in 30 ml of THF, cooled to −60° C. and admixed with 0.40 ml of n-butyllithium (2M in pentane, 0.8 mmol). The solution is allowed to come to room temperature and after a further 5 minutes is again cooled to −60° C. and admixed with 147 mg of zirconium tetrachloride·2THF (0.39 mmol). The reaction mixture is refluxed for 3 hours, the solvent is subsequently drawn off, the residue is washed with n-hexane and filtered through a Schlenk tube. The residue is dissolved in diethyl ether and filtered. After removal of the solvent, 311 mg of product can be isolated. (80% of theory)

IR (KBr): 2964m; 2920w; 1600b,m; 1500w; 1493w; 1461w; 1439w; 1412w; 1262s; 1106vs; 1067vs; 1021vs; 845s; 803vs; 760vs; 511m; 488m; 465m, 448m.

Microprobe: C, Fe, Si, Zr in a consistent elemental ratio.

EXAMPLE IV

Bis(9-ferrocenylfluorenyl)titaniumdichloride 214 mg of 9-ferrocenylfluorene (0.61 mmol) (M. Buchmeiser, H. Schottenberger, *Organometallics*, 12, 2472 (1993)) are dissolved in 20 ml of THF, cooled to −60° C. and admixed with 0.40 ml of n-butyllithium (1.6M in hexane, 0.64 mmol). The solution is warmed to room temperature, stirred for a further 15 minutes, again cooled to −60° C. and 105 mg of titanium tetrachloride.2THF (0.31 mmol) are added. After stirring for 2 hours at room temperature, all the solvent is drawn off in vacuo, the residue is digested in n-hexane and the solution is filtered through a Schlenk tube. After removal of the solvent in vacuo, 199 mg of product can be isolated from the hexane solution. (80% of theory)

IR (KBr): 3365b,m; 2960m; 2927m; 2855w; 1629b,m; 1449m; 1412w; 1262vs; 1098b,vs; 1025b,vs; 874b,m; 805vs; 745m; 480w.

$^1$H-NMR (CDCl$_3$, TMS): 4.17 ppm(s, 10H); 4.74 ppm (t, 4H); 5.35 ppm(t, 4H); 8.24 ppm(m), $^{13}$C-NMR (CDCl$_3$, TMS): 67.9 ppm; 68.2 ppm; 72.9 ppm; 118.6 ppm; 124.1 ppm; 126.7 ppm; 127.0 ppm.

MS (EI, 70 eV): m/e=761 (M$^+$−56 (Fe), 3%); 696 (M$^+$−121 (FeCp), 15%); 632 (M$^+$−185 (fec), 1.5%); 575 (M$^+$−242 (2 FeCp), 7.5%); 349 (ferrocenylfluorenyl radical cation·100%)

Microprobe: C, Fe, Ti in a consistent elemental ratio.

EXAMPLE V rac-(Ferroceno[2,3]inden-1-yl)dimethylsilylene(cyclopentadienyl)zirconium dichloride

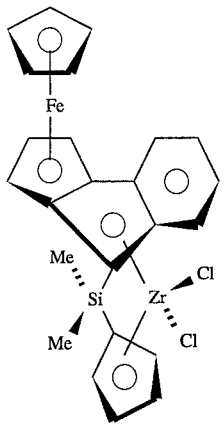

0.205 g of ferroceno[2,3]indene (M. Cais, A. Modiano, A. Raveh, *J. Am. Chem. Soc.*, 87, 5607 (1965)) (0.75 mmol) is dissolved in 20 ml of THF, cooled to −80° C. and admixed with 0.28 ml of n-butyllithium (2M in pentane). The solution is warmed to room temperature, again cooled to −80° C. and 1.15 ml of dimethyldichlorosilane (8.9 mmol) are added. The solution suddenly becomes yellow. All solvent is then drawn off in vacuo. After the residue has been again dissolved in 20 ml of THF and cooled to −80° C., 0.40 ml of a solution of sodium cyclopentadienide in THF (2M) is added. The solution is again warmed to room temperature, cooled in turn to −80° C. and 0.80 ml of n-butyllithium (2M in pentane) is added. After warming to room temperature to complete the deprotonation reaction, 285 mg of zirconiumtetrachloride·2THF (0.75 mmol), dissolved in 40 ml of THF, are added at −50° C. After warming to room temperature, the solution is heated at 65° C. for 2 hours, then stirred for 18 hours at room temperature and also treated for 45 minutes with ultrasound. The solvent is drawn off, the residue is dissolved in n-hexane and filtered through a Schlenk tube. After removal of the solvent in vacuo, 374 mg of product (90% of theory) can be isolated. According to the mass spectrum, this also contains traces of the compound III (m/e=604).

IR (KBr): 3095w; 2925m; 1607m; 1495m; 1465m; 1439m; 1414m; 1262vs; 1169m; 1110b,vs; 1019b,vs; 955s; 801b,vs; 760s; 731s; 488m; 463m; 448m; 403m.

MS (EI, 120° C., 10$^{-7}$ torr): m/e=429 (2.6%); 388 (100%); 331 (19.9%, ferroceno[2,3]inden-1-yl-dimethylsilylene radical cation); 316 (2.6%, ferroceno[2,3]inden-1-yl-methylsilylene radical cation); 301 (2.5%, ferroceno[2,3]inden-1-yl-silylene radical cation); 273 (26.0%, ferroceno[2,3,a]inden-1-yl radical cation)

Microprobe: C, Fe, Si, Zr in a consistent elemental ratio.

EXAMPLE VI

Bis(4-ferrocenylferroceno[2,3]cyclopentadienyl)dimethylsilylenezirconium dichloride (diastereomeric mixture)

300 mg (0.74 mmol) of 2-ferrocenylferroceno[3,4]cyclopenta-1,3-diene (T. S. Abram, W. E. Watts, *J. Chem. Soc., Perkin I*, 1531 (1977)) are dissolved in 30 ml of THF and admixed at −50° C. with 0.46 ml of n-butyllithium (1.6M in hexane, 0.74 mmol). After 5 minutes, 0.50 ml of dimethyldichlorosilane (0.4 mmol) is added. After the reaction solution has been warmed to room temperature, 0.46 ml of n-butyllithium (see above) is again added at −50° C. After again warming to room temperature and cooling to −50° C., 140 mg of zirconium tetrachloride. 2THF (0.37 mmol) are added. The reaction mixture is refluxed for 1 hour. It is subsequently evaporated to dryness and the residue is extracted with diethyl ether (1st fraction) and methylene chloride (2nd fraction). Each of the fractions gives a greenish amorphous powder. The 1st fraction represents the diastereomeric target structures. Fraction 2 mainly contains only oligomeric products. Yield: 150 mg (40% of theory)

$^1$H-NMR (CDCl$_3$, TMS): 3.4–4.3 ppm, ferrocene region $^{13}$C-NMR (CDCl$_3$, TMS): −0.2 ppm; 68.3 ppm; 69.5 ppm.

MS (EI, 70 eV), the assignable fragmentations are given in brackets: m/e=846.5 (M$^+$−185 (Fc), 32%); 818.5 (M$^+$−214 (Fc-Si), 54%); 696.5 (M$^+$−336 (Fc—FeCp—Si), 33%); 620.0 (M$^+$−412.5 (2 Fc, SiCH$_3$), 100%); 605.0 (M$^+$−427.5 (2 Fc, Si(CH$_3$)$_2$, 29%); with Fc=ferrocenyl, Cp=cyclopentadienyl.

Microprobe: C, Fe, Cl, Si, Zr in a consistent elemental ratio.

EXAMPLE VII rac-(Ferroceno[2,3]inden-1-yl)dimethylsilylene(t-butylamido)zirconium dichloride 400 mg of ferroceno[2,3]indene (M. Cais, A. Modiano, A. Raveh, *J. Am. Chem. Soc.*, 87, 5607 (1965)); 1.46 mmol) are dissolved in 50 ml of diethyl ether and admixed at −50° C. with 0.95 ml of n-butyllithium (1.6M in hexane, 1.52 mmol). After the solution has been warmed to room temperature and again cooled to −50° C., 2.0 ml of dimethyldichlorosilane (15 mmol), dissolved in 70 ml of diethyl ether, are added. After all solvent and the excess of dimethyldichlorosilane have been drawn off in vacuo, the residue is suspended in THF:diethyl ether=20:80 and admixed with a solution of t-butylamide in 50 ml of diethyl ether, prepared from 16 ml of t-butylamine and 0.95 ml of n-butyllithium (see above). After stirring for 4 hours, 1.90 ml of n-butyllithium (1.6M in hexane, 3.04 mmol) are added at −60° C. The mixture is warmed to room temperature, again cooled to −60° C. and 550 mg of zirconium tetrachloride (1.46 mmol) are added. The reaction mixture is subsequently refluxed for 1 hour. After removal of the solvent, the residue is dissolved in diethyl ether and filtered through a Schlenk tube. Finally, the ether is drawn off in vacuo. The target compound is a deep orange powder. Yield: 780 mg (95% of theory)

IR (KBr): 3462 b,s; 2971vs; 2923s; 2892vs; 2798vs; 2696m; 2586s; 2487m; 2034m; 1634b,m; 1609m; 1505m; 1476m; 1466m; 1428m; 1403m; 1378s; 1301m, 1262m, 1216m, 1106m, 1019m; 1001w; 802b,m; 760m; 448b,w.

$^1$H-NMR (CDCl$_3$, TMS): t-butyl- and SiMe$_2$ region: 1.00–1.54 ppm (m, 12H); 1.78 ppm (bs, 3H); ferrocene region: 3.76 ppm(s, 5H); 4.04 ppm("t", 1H); 4.39 ppm(dxd, 1H); 4.43 ppm(dxd, 1H); aromatic region: 7.00–7.36 ppm (m, 4H)

$^{13}$C-NMR (CDCl$_3$, TMS): t-butylamido region: 25.53 ppm; 31.30 ppm; 32.97 ppm; ferrocene region: 58.79 ppm; 63.11 ppm; 69.48 ppm; 70.18 ppm; quaternary ferrocene C 92.29 ppm, 72.74 ppm; aromatic region: 120.11 ppm; 124.55 ppm; 125.08 ppm; 126.55 ppm; quaternary aromatic C 142.11 ppm, 147.26 ppm.

MS (EI, 70 eV).: m/e=548.5 (M$^+$–15(CH$_3$), 2%); 412.5 (M$^+$–151 (CpFe, 2 CH$_3$), 6%); 384.0 (M$^+$–180.5 (CpFe, Si(CH$_3$)$_2$, 10%); 327 (M$^+$–236 (CpFe, Si(CH$_3$)$_2$, t-butyl, 100%); 272 (ferrocenoindenyl), 47%)

Microprobe: C, Fe, N, Cl, Si, Zr in a consistent elemental ratio.

EXAMPLE VIII rac-(Ferroceno(2,3)inden-1-yl)dimethylsilylene(tetramethylcyclopentadiene)zirconium dichloride A) Synthesis of 2,3,4,5-tetramethylcyclopentadienyldimethylchlorosilane (D. Stern, M. Sabat, T. J. Marks, *J. Am. Chem. Soc.* 112 (1990) 9558)

4.0 g (32.8 mmol) of 1,2,3,4-tetramethylcyclopentadiene (F. X. Kohl; P. Jutzi, *J. Organomet. Chem.* 243 (1983) 119–121; G. Schmitt, S. Özman, Chemikerzeitung 100 (1976), 143; E. E. Bunel; P. Campos, J. Ruz; L. Valle, Organometallics 7 (1988), 1828–1838; C. M. Fendrick; L. D. Schertz; V. W. Day; T. J. Marks, Organometallics 7, (1988) 1828–1838 and literature cited therein) are dissolved in 50 ml of absolute THF and admixed with 21 ml of n-butyllithium (1.6M in pentane, 33.6 mmol). The mixture is stirred for 2 hours and 4.50 g (33.3 mmol) of dimethyldichlorosilane, dissolved in 30 ml of absolute THF, are then added dropwise at 0° C. The mixture is subsequently stirred for a further 20 hours. After removal of the solvent in vacuo and filtering off the lithium chloride formed during the reaction, the residue is vacuum distilled. Bp: 57°–65° C. (P=0.1 torr).

Yield: 3.0 g (42% of theory). The pale yellow compound is stored at –18° C.

B) 2-Ferrocenylbenzoic acid (M. Cais, A. Modiano, A. Raveh, *J. Am. Chem. Soc.*, 87, 5607 (1965); R. C. Kerber, D. J. Entholt, *Synthesis*, 449 (1970); T. Lanez, P. L. Pauson, *J. Chem. Soc. Perkin* 1, 2437 (1990 ))

27.27 g of anthranilic acid (0.20 mol) are suspended in 500 ml of half-concentrated hydrochloric acid (5M) and a solution of 19.68 g of sodium nitrite (0.20 mol) in 150 ml of water is slowly added dropwise with ice cooling. During the dropwise addition, the temperature of the reaction mixture does not exceed 0° C. A clear yellow diazonium solution is formed, and this is stirred further for about half an hour at 0° C. Subsequently, the solution is pneumatically added dropwise to a solution of 44.65 g of ferrocene (0.24 mol) and 0.81 g of acetonitrile (0.02 mol) in 500 ml of toluene with vigorous stirring. The reaction mixture is stirred overnight at room temperature. After addition of about 2 g of sodium hyposulfite to reduce ferrocenium ions, it is extracted four times with 200 ml each time of diethyl ether.

The combined organic phases are extracted three times with 100 ml each time of 2N ammonia. The ammoniacal solution is quenched by pouring onto ice/hydrochloric acid, and the main product 2-ferrocenylbenzoic acid and also the by product 1,1'-bis(2-carboxyphenyl)ferrocene are extracted three times with 100 ml each time of diethyl ether.

After drawing off the ether, 49.62 g of crude product (2-ferrocenylbenzoic acid and 1,1'-bis(2-carboxyphenyl)ferrocene) are isolated.

The crude product is dissolved in diethyl ether and adsorbed on about 25 g of silica (FLUKA 60741). Diethyl ether is removed in vacuo and 2-ferrocenylbenzoic acid is isolated by continuous extraction in a Soxhlet apparatus using 300 ml of petroleum ether 50/70. After removal of the petroleum ether in vacuo, the product is obtained as a pale orange powder.

Yield: 35.4 g of 2-ferrocenylbenzoic acid (58.1% of theory)

C) Ferroceno[2,3]inden-1-one (M. Cais, A. Modiano, A. Raveh, *J. Am. Chem. Soc.*, 87, 5607 (1965); R. C. Kerber, D. J. Entholt, *Synthesis*, 449 (1970); T. Lanez, P. L. Pauson, *J. Chem. Soc. Perkin* 1, 2437 (1990))

In a Schlenk flask having a mercury valve, 20.00 g of 2-ferrocenylbenzoic acid (65.3 mmol) are dissolved in 400 ml of absolute methylene chloride and cooled to 0° C. 14.30 g of phosphorus pentachloride (68.6 mmol) are added and, after equilibrating to room temperature for about half an hour, the mixture is refluxed for about 2 hours until a violet coloration appears. After again cooling to 0° C., 9.15 g of aluminum trichloride (68.6 mmol) are carefully added, the mixture is then again warmed to room temperature and stirred for about 1 hour. After quenching the reaction mixture in ice-cooled aqueous citric acid solution (29 g, 2 mol equivalents based on AlCl$_3$), it is repeatedly extracted with diethyl ether, the combined ether phases are dried over sodium sulfate, filtered and, after addition of about 40 g of silica gel (Fluka 60741), the solvent is drawn off.

The residue is subjected to continuous Soxhlet extraction using 500 ml of petroleum ether (50°–70° C.). On cooling the solvent, R,S-ferroceno[2,3]inden-1-one crystallizes after seeding in the form of violet needles. A further, often oily yield (up to 17%) is obtained on evaporation of the mother liquor.

Yield: 10.41 g of ferroceno[2,3]inden-1-one (55.3% of theory) as crystalline product, 3.20 g of ferroceno[2,3]inden-1-one (17.0% of theory) as oily product D) Ferroceno[2,3]inden-1-ol (M. Cais, A. Modiano, A. Raveh, *J. Am. Chem. Soc.*, 87, 5607 (1965); R. C. Kerber, D. J. Entholt, *Synthesis*, 449 (1970))

6.531 ml of SMEAH (sodium bis(2-methoxyethoxy)aluminumdihydride, 80% in toluene, 23.33 mmol, 1.2 mol equivalents) are dissolved in 50 ml of absolute toluene and placed in a Schlenk flask. 6.112 g of ferrocenoindenone (21.2 mmol) are likewise dissolved in about 50 ml of absolute toluene and transferred to a dropping funnel. While stirring vigorously, it is then slowly added dropwise over a period of 1 hour so that the slightly foaming system does not heat up above room temperature.

After stirring overnight, the system is quenched with ice, acidified with dilute hydrochloric acid (2M) and extracted three times with 50 ml each time of diethyl ether. The combined organic phases are dried over sodium sulfate and the solvent is drawn off in vacuo. 5.983 g of R,S-ferroceno [2,3]inden-1-ol remain as oily product.

Yield: 5.983 g (92.87% of theory)

E1) Ferroceno[2,3]ind-1-ene via 2e⁻ reduction 1.90 g of ferroceno[2,3]inden-1-ol (isomer mixture, 6.6 mmol) are dissolved in 50 ml of absolute diethyl ether, cooled to −25° C. and admixed with 1.80 ml of tetrafluoroboric acid (54% in diethyl ether, 13.1 mmol) over a period of 5 minutes. While stirring, the mixture is allowed to come to room temperature. The solution is then filtered through a Schlenk tube, the residue is washed with diethyl ether and dried in vacuo. Yield: 1.98 g (84% of theory)

IR (KBr): 3402b, vs; 3102m; 1634m; 1495m; 1422m, 1306m; 1084b,vs; 1059b,vs; 853s; 771s; 744.8m; 694.63m; 534s; 521s; 480m.

MS (FAB): m/e=273.0 (100%); 545.9 (18%)

600 mg of sodium are dissolved in 30 ml of $NH_{3(l)}$, diluted with 30 ml of absolute diethyl ether and added to a suspension of 1.424 g of ferroceno[2,3]indenium tetrafluoroborate (3.96 mmol) in 30 ml of absolute THF, cooled to −50° C. The reaction mixture is allowed to come to room temperature and poured into 150 ml of saturated ammonium chloride solution. It is then extracted with diethyl ether, dried over sodium sulfate and, after removal of the solvent, the residue is flash-chromatographed over silica G-60 (Fluka, 220–440 mesh; column dimensions: 30×4 cm; mobile phase: n-hexane: diethyl ether=50:50). The compound can be obtained as broad bands which are difficult to separate. Residual impurities are removed by column chromatography (stationary phase: silica G-60, 220–440 mesh, Fluka; mobile phase: n-hexane, column dimensions: 3.5×80 cm; flow rate 40 ml/min).

Yield: 1.09 g (60% of theory)

IR (KBr): 3097w; 3074w; 3056w; 3008w; 2914m; 2894m; 2819w; 1771w; 1719m; 1640m; 1623m; 1609m; 1497s; 1466m; 1443m; 1420s; 1360m; 1304m; 1260m; 1223m; 1173m; 1123s; 1106vs; 1052s; 1042s; 1021s; 1000vs; 949m; 878s; 861m; 832vs; 807vs; 762vs; 722vs; 648m; 577m; 542s; 511vs; 486vs; 465vs; 440vs; 426m.

$^1$H-NMR (CDCl$_3$, TMS): 3.50 ppm, (d, 1H J=20.1 Hz); 3.66 ppm, (d, 1H J=20.1 Hz); 3.78 ppm, (s, 5H), 4.08 ppm, (t, 1H), 4.39 ppm, (d, 1H, j=3.05 Hz), 4.44 ppm, (d×d, 1H, J=2.29 Hz, J=0.91 Hz), 7.0–7.4 ppm, (m, 4H)

$^{13}$C-NMR (CDCl$_3$; TMS): 32.9; 58.8; 63.1; 69.4; 70.1; 92.3; 92.7; 120.1; 124.5; 125.0; 126.5; 142.1; 147.3 ppm.

MS (EI, 70eV): m/e=274M+. (100%), 209 (12%), 153 (54%), 121 (15%)

E2) Ferroceno[2,3]ind-1-ene by catalytic hydrogenation

Ferroceno[2,3]ind-1-ene (7.00 g; 24.3 mmol) is dissolved in 100 ml of glacial acetic acid, added to a 2 l hydrogenation reactor and rinsed in using 50 ml of glacial acetic acid. Subsequently, 7.0 g of Pd/C catalyst (5%, Fluka 75992) are added together with a further 50 ml of glacial acetic acid. The reactor is closed, heated to 30° C. and pressurized with 10 bar of H$_2$ at a stirring rate of 400 rpm. After 11 hours at 30° C., the reactor is cooled to room temperature and the reaction solution is drained. After the reactor has been rinsed out 3 times with 100 ml each time of n-hexane, the solutions are combined, the catalyst is filtered off and washed (once with 50 ml of glacial acetic acid and 3 times with 50 ml each time of n-hexane). The solution is then diluted with 1200 ml of water and extracted in a separating funnel. The aqueous phase is subsequently extracted repeatedly with 50 ml each time of n-hexane (until the aqueous phase is virtually colorless). The organic phases are combined, washed twice with 100 ml each time of saturated sodium hydrogen carbonate solution and once with 100 ml of water, dried using Na$_2$SO$_4$, filtered and the solvent is drawn off in a water pump vacuum.

The residue is separated by column chromatography (eluant: n-hexane; stationary phase: Kieselgel 60 (Fluka 60738); column dimensions: 25×4 cm).

Yield: 4.75 g of ferroceno[2,3]ind-1-ene, (rac-4H-indeno [2,3]ferrocene) (71.3% of theory)

F) Reaction to give rac-(ferroceno[2,3]inden-1-yl)dimethylsilylene(tetramethylcyclopentadienyl)zirconium dichloride 0.25 g (0.912 mmol) of ferroceno[2,3]ind-1-ene is dissolved in 30 ml of absolute THF, cooled to −60° C. and admixed with 0.60 ml of n-butyllithium (1.6M in pentane, 0.96 mmol). The reaction solution is allowed to stand until room temperature is reached and is subsequently stirred for a further 30 minutes. 0.25 ml of 1-(chlorodimethylsilylene)-2,3,4,5-tetramethylcyclopentadiene (1.2 mmol) is then added dropwise by means of a 1 ml syringe. During this procedure, the solution changes its color from red to orange. After 1 hour, all the solvent is drawn off in vacuo, with excess silyl reagent also being removed. The residue is subsequently dissolved in 30 ml of absolute THF, cooled to −30° C., admixed with 1.20 ml of n-butyllithium (1.6M in pentane, 1.92 mmol) and, after warming to room temperature, stirred for 5 minutes. During this procedure, the solution changes color to deep violet. After cooling to −50° C., a solution of 350 mg of zirconium tetrachloride.2THF in 30 ml of absolute THF is added dropwise. The reaction mixture is subsequently refluxed for 3 hours. The solvent is then drawn off in vacuo, the residue is taken up in absolute n-hexane and filtered through a Schlenk tube. Subsequent crystallization at −18° C. allows the isolation of 430 mg of product (77% of theory).

IR (KBr): 3100w; 2961s; 2930s; 2874m; 1646w; 1609w; 1491w; 1473w; 1460w; 1420w; 1412w; 1378m; 1261s; 1105vs; 1021b,s; 802b,vs; 761w; 490m.

$^1$H-NMR (CDCl$_3$, TMS): −0.5–2.5 ppm, methyl groups, 18H 9; 3.7–4.7 ppm (ferrocene part, 7H); 6.8–7.6 ppm (aromatic part, 4H).

$^{13}$C-NMR (CDCl$_3$, TMS): −0.25 ppm; −0.20 ppm; 0.38 ppm; 1.0 ppm; 12.6 ppm; 13.1 ppm; 13.9 ppm; 16.0 ppm; 18.2 ppm; 18.6 ppm; 22.9 ppm; 25.5 ppm; 26.5 ppm; 33.3 ppm; 35.0 ppm; 38.0 ppm; 45.0 ppm; 57.8 ppm; 58.8 ppm; 61.0 ppm; 63.5 ppm; 64.8 ppm; 68.2 ppm; 69.4 ppm; 69.9 ppm; 70.2 ppm; 91.0 ppm; 91.5 ppm; 119.8 ppm; 119.9 ppm; 120.0 ppm; 123.6 ppm; 124.1 ppm; 124.5 ppm; 125.4 ppm; 126.6 ppm; 140.5 ppm; 141.5 ppm.

MS (EI, 70eV): m/e=545 (M$^+$—65 (Cp), <1%); 509 (M$^+$—101 (CpCl), <1%); 473 (M$^+$—137 (CpCl$_2$), <1%); 489 (M$^+$—121 (CpFe), <1%); 454 (M$^+$—156 (CpFeCl), 6%); 369 (M$^+$—241 (CpFeCp*), 20%); 274 (M$^+$—336, 100%)

Microprobe: C, Fe, Cl, Zr, Si in a consistent elemental ratio.

EXAMPLE IX rac-(Ferroceno[2,3]inden-1-yl)dimethylsilylene(fluoren-9-yl)zirconium dichloride 0.26 g (0.948 mmol) of ferroceno[2,3]indene is dissolved in 30 ml of THF, cooled to −70° C. and admixed with 0.62 ml of n-butyllithium (1.6M in hexane, 1.00 mmol). The mixture is allowed to come to room temperature and stirred for a further 30 minutes. It is subsequently again cooled to −70° C. and 5 ml of dimethyldichlorosilane (41.5 mmol) are added by means of a syringe. The solution suddenly changes color to orange. All the solvent is then drawn off in vacuo, with excess dimethyldichlorosilane also being removed. The residue is dissolved in 30 ml of THF, cooled to −70° C. and admixed with 5.20 ml of lithium fluorenide solution (0.2M in THF, 1.04 mmol). The cold bath is removed and the mixture is left stirring for 40 minutes at room temperature. It is then once again cooled to −70° C., 1.25 ml of n-butyllithium (1.6M in hexane, 2.0 mmol) are added and the mixture is again brought to room temperature. During this procedure, the solution changes color to deep red. The solution is again cooled to −70° C. and admixed with 0.360 g of zirconium tetrachloride. 2THF, dissolved in 30 ml of THF. After warming to room temperature, the solution is boiled under reflux for 2.5 hours and stirred for 90 hours at room temperature. The solvent is drawn off in vacuo, the residue is dissolved in n-hexane and filtered through a Schlenk tube. After removal of the solvent, 260 mg of product can be isolated (42% of theory).

IR (KBr): 3392b,s; 3062w; 2962s; 2925s; 2856m; 1694m; 1607m; 1463m; 1449m; 1439m; 1262vs; 1106b,vs; 1021vs; 803vs; 758m; 741m; 556m; 509m; 480m.

$^1$H-NMR (CDCl$_3$, TMS): dimethylsilylene groups: −0.2–0.4 ppm; ferrocene part: 4.0 ppm(s, 5H); 4.05 ppm (d, 1H); 4.2 ppm ("t", 1H); 4.25 ppm (d, 1H); aromatic part: 6.9–7.9 ppm(12H).

$^{13}$C-NMR (CDCl$_3$, TMS): dimethylsilylene region: −4.40 ppm; −3.86 ppm; Ferrocene region: 69.39 ppm; 69.64 ppm; 69.80 ppm; 70.07 ppm Aromatic region: 119.84; 120.23; 120.30; 120.87; 124.40; 124.54; 124.60; 124.77; 125.00; 125.11; 125.61; 125.78; 126.29; 126.51; 126.64; 126.68; 127.39 ppm

EXAMPLE X o,o'-Bis(ferroceno[2,3]inden-1-yl)biphenylenezirconium dichloride

A) Reaction of rac-ferroceno[2,3]inden-1-one with dilithiobiphenyl-TMEDA 0.88 g of dilithiobiphenyl-TMEDA (3.17 mmol) (W. Neugebauer, A. J. Kos, P. v. Rague Schleyer, *J. Organomet. Chem*, 228, 107 (1982)) is dissolved in 50 ml of THF and admixed at −70° C. with 1.80 g of ferroceno[2,3]inden-1-one (6.47 mmol), dissolved in 30 ml of THF. The reaction mixture is warmed to room temperature and is finally poured into saturated ammonium chloride solution. After repeated extraction with diethyl ether, the residue after removal of the solvent is chromatographed. (Silica G-60, 220–440 mesh, Fluka; n-hexane: diethyl ether=80:20; column dimensions 90×4 cm; flow rate: 25 ml/min, amount applied: in each case about 0.4 g of mixture). The following compounds can be obtained in pure form:

1st fraction: o,o'-bis (1-hydroxyferroceno[2,3]inden-1-yl)biphenyl, meso form

IR(KBr): 3402w; 3056w; 2925w; 1636w; 1493w; 1443w; 1393w; 1332w; 1264s; 1119b,vs; 1106b,vs; 1036vs; 1023vs; 1000s; 955s; 880m; 812b,vs; 749s; 710s; 492m; 477m; 467m; 419w.

$^1$H-NMR (CDCl$_3$, TMS): 3.15 ppm (m, 2H), 3.96 ppm (s, 10H), 4.05 ppm (m, 2H), 4.11 ppm, (m, 2H), 6.04 ppm (d, 2H, J=8 Hz), 6.58–7.60 ppm (m, 14H), 8.23 ppm (d, 2H, J=8 Hz)

$^{13}$C-NMR (CDCl$_3$, TMS): 59.85; 62.76; 69.24; 69.91; 91.61; 105.83; 120.19; 124.44; 125.21; 125.92; 126.11; 126.57; 126.93; 127.12; 127.21; 127.80; 128.72; 129.23; 131.40; 139.32; 139.89; 140.68; 141.21; 155.07 ppm.

MS (EI, 70 eV): m/e=732.5 (M$^+$., 1%) 714.0 (M$^+$−18, 2%), 698.0 (M$^+$−34, 1.5%), 444.0 (M$^+$−288, 100%), 306.0 (M$^+$−426, 80%)

2nd fraction: o,o'-bis (1-hydroxyferroceno[2,3]inden-1-yl)biphenyl

IR(KBr): 3500b,w; 2966w; 1607w; 1474w; 1414w; 1260s; 1011vb,vs; 910m; 864s; 789b,vs; 758vs; 700vs; 644m; 612w; 581w; 554m; 506s; 463s.

$^1$H-NMR (CDCl$_3$, TMS): 3.97 ppm (s, 5H), 4.14 ppm (s, 5H), 4.23 ppm (m, 2H), 4.32 ppm (m, 2H), 4.58 ppm (m, 1H), 4.63 ppm (m, 1H), 6.58–6.64 ppm (m), 7.03–7.34 ppm (m).

$^{13}$C-NMR (CDCl$_3$, TMS): 59.54; 59.87; 60.04; 60.26; 65.83; 69.81; 70.03; 82.18; 82.83; 89.82; 90.91; 103.17; 105.41; 119.67; 119.95; 120.33; 124.33; 125.48; 126.07; 126.42; 126.88; 128.14; 128.29; 131.22; 131.30; 131.79; 138.84; 139.76; 140.44; 141.43; 141.89; 142.35; 143.29; 155.25; 155.60; 156.19 ppm.

MS (EI, 70 eV): m/e=732.5 (M$^+$., 67%) 714 0 (M$^+$−18, 100%), 698.0 (M$^+$−34, 30%), 455.5 (M$^+$−277, 33%), 441.5 (M$^+$−290, 69%), 305.5 (M$^+$−426, 81%)

3rd fraction: o,o'-bis(1-hydroxyferroceno[2,3]inden-1-yl)biphenyl

IR(KBr): 2965w; 1607w; 1484w; 1432w; 1262s; 1110b, vs; 1019b,vs; 801vs; 758vs; 739vs; 700vs; 609w; 577w; 554w; 506s; 461m; 413m.

$^1$H-NMR (CDCl$_3$, TMS): 3.92 ppm, (s, 5H), 4.01 ppm, (s, 1H), 4.10 ppm, (s, 2H), 4.17 ppm, (m, 2H), 4.19 ppm, (m, 2H), 4.45 ppm, (m, 1H), 4.54 ppm, (m, 1H), 6.52–7.55 ppm, (m, 16H)

$^{13}$C-NMR (CDCl$_3$, TMS): 59.84; 60.09; 61.93; 69.37; 69.59; 70.00; 70.38; 78.43; 82.89; 89.62; 90.83; 100.63; 104.98; 119.94; 120.40; 123.14; 124.70; 125.64; 126.10; 127.07; 127.17; 128.01; 128.67; 131.89; 141.13 ppm.

MS (EI, 70 eV): m/e=732.5 (5%), 714.5 (5%), 443.5 (35%), 347.5 (39%), 305.5 (100%)

Total yield (fraction 1–3): 1.63 g (71.5% of theory)

4th fraction: ferroceno[2,3]inden-1-one (50 mg)

B) Formation of the dication 1.63 g of o,o'-bis(1-hydroxyferroceno[2,3]inden- 1-yl)biphenyl (diastereomeric mixture, 2.23 mmol) are dissolved in 50 ml of methylene chloride, admixed with 10 ml of propionic anhydride and, after addition of 1 ml of tetrafluoroboric acid (54% in diethyl ether, 7.30 mmol), stirred for 15 minutes. The dication formed is precipitated with 200 ml of diethyl ether and filtered through a Schlenk tube. After drying in a high vacuum, 1.90 g (98% of theory) of o,o'-bis(ferroceno[2,3,a]coindenium)biphenyl ditetrafluoroborate can be isolated.

IR (KBr): 3438vb,vs; 2925m; 2856m; 1638b,m; 1418w; 1262w; 1084vb,vs; 841m; 807w; 744w; 520w; 477w.

C) Reduction with Na/ammonia 700 mg of sodium (30 mmol) are dissolved in about 100 ml of NH$_3$(l). This solution is subsequently added at −50° C. to a solution of 1.90 g of the above described dication (2.18 mmol) in 50 ml of THF. The deep red reaction mixture is brought to room temperature, and after all of the ammonia has evaporated, poured into saturated ammonium chloride solution and extracted with diethyl ether. If desired, the aqueous phase can be brought to a pH of 5 using acetic acid. The combined organic phases are dried over sodium sulfate. The residue is, after removal of the diethyl ether, flash-chromatographed. (Silica G 60, 220–440 mesh, Fluka, n-hexane: diethyl ether=75:25, column dimensions: 3×20 cm). Yield: 1.115 g (73% of theory)

IR (KBr): 3054m; 3018m; 2923m; 1609b,m; 1559w; 1497m; 1476m; 1464m; 1441m; 1295w; 1108vs; 1007b, s; 911s; 803s; 733vs; 650w; 556m; 509m; 481m; 461m; 442m.

$^1$H-NMR (CDCl$^3$, TMS): 3.2–5.1 ppm, m, ferrocene part 6.2–7.6 ppm, m, aromatic part $^{13}$C-NMR (CDCl$_3$, TMS): 58.16; 58.35; 58.77; 61.80; 61.89; 62.32; 62.98; 63.49; 69.19; 69.24; 69.3; 69.63; 70.07; 70.20; 76.32; 76.96; 77.17; 77.59; 91.30; 98.96; 118.11; 119.80; 119.97; 120.32; 120.61; 124.77; 125.00; 125.13; 125.37; 125.68; 125.78; 126.16; 126.68; 126.86; 126.99;

127.15; 127.25; 127.34; 128.00; 128.24; 129.08; 129.18; 130.08; 130.21; 130.68; 130.85; 131.11; 139.65; 140.66; 140.85; 141.45; 141.71; 142.21; 150.38; 153.07 ppm.

MS (EI, 70 eV): m/e=596 (15%), 410 (47%), 205 (100%)

D) o,o'-Bis(ferroceno[2,3]inden-1-yl)biphenylenezirconium dichloride (diastereomeric mixture)

342 mg of o,o'-bis(ferroceno[2,3]inden-1-yl)biphenyl (0.489 mmol) are dissolved in 50 ml of THF, cooled to −50° C. and admixed with 0.61 ml of n-butyllithium (1.6M in hexane, 0.976 mmol). After briefly warming to room temperature, the solution is again cooled to −50° C. and 250 mg of zirconium tetrachloride.2THF (0.663 mmol) are added. The reaction mixture is refluxed for 1 hour. After removal of the solvent, the residue is dissolved in diethyl ether, filtered through a Schlenk tube and finally evaporated in vacuo. Ether filtrates can still contain traces of LiCl. Yield: 416 mg (99% of theory).

IR (KBr): 3436b,s; 1634b,s; 1499m; 1476m; 1465m; 1439m; 1295w; 1262vs; 1165w; 1106b,vs; 1019vs; 878w; 803vs; 758vs; 717m; 556m; 509m. 1H-NMR (CDCl$_3$, TMS): 3.50–5.1 ppm, m, ferrocene part, of which 3.70 ppm, s, 3.76 ppm, s, 6.8–7.6 ppm, m.

$^{13}$C-NMR (CDCl$_3$, TMS): 58.38; 58.80; 61.92; 62.33; 63.00; 63.53; 69.21; 69.28; 69.34; 69.65; 70.09; 70.22; 98.98; 119.82; 120.00; 120.35; 120.65; 125.04; 125.17; 125.39; 125.48; 125.70; 125.79; 126.18; 126.36; 126.71; 126.90; 127.03; 127.17; 127.28; 127.36; 128.26; 129.10; 129.19; 129.36; 130.11; 130.70; 130.89; 131.12; 139.69; 140.68; 140.86; 141.49; 142.22; 150.40; 153.09 ppm.

MS (EI, 70 eV): m/e=661 (M$^+$−198, 100%), 633 (M$^+$−226, 10%), 511 (M$^+$−348, 14%)

Elemental analysis: Fe, Cl, C, Zr in a consistent elemental ratio.

POLYMERIZATION EXAMPLES

EXAMPLE 1

A 2 l stirred reactor is made inert at room temperature using 11.2 g of 10% strength MAO (methylaluminoxane, Witco, FRG) and then charged with 300 g of liquid propylene and the mixture is stirred for 15 minutes.

10 mg of rac-(ferroceno[2,3]inden-1-yl)dimethylsilylene(cyclopentadienyl)zirconium dichloride are dissolved in 5.9 ml of toluene and mixed with 11.2 g of 10% strength MAO. The catalyst solution is subsequently rinsed into the reactor using a further 200 g of propylene and the mixture is heated to the polymerization temperature of 70° C. which is kept constant for a period of two hours. The reaction is stopped after two hours by flashing the propylene. 151.1 g of polypropylene having a molecular weight M$_w$=6000 g/mol and a polydispersity M$_w$/M$_n$=3.0 were obtained.

EXAMPLE 2

A 2 l stirred reactor is made inert at room temperature using 3.9 g of 10% strength MAO and then charged with 500 g of liquid propylene, the mixture is stirred for 15 minutes and subsequently heated to 70° C. 5 mg of bis(ferroceno[2,3]inden-1-yl)dimethylsilylenezirconium dichloride are dissolved in 10.4 ml of toluene and mixed with 3.9 g of 10% strength MAO. The catalyst solution is injected into the reactor with ethylene. An ethylene partial pressure of 2 bar is maintained over the reaction time of two hours. The reaction is stopped by flashing the monomers. 0.8 g of an ethylene/propylene copolymer having a molecular weight M$_w$=42,000 g/mol and a polydispersity M$_w$/M$_n$=2.8 was obtained. The propylene content is 37 mol %.

EXAMPLE 3

A 2 l stirred reactor is made inert under nitrogen, 10.8 g of 10% strength MAO and 1 dm$^3$ of n-hexane are then metered in and the mixture is stirred for 15 minutes. After degassing the suspension medium and heating the reactor to the reaction temperature of 70° C., the polymerization is started by injecting the catalyst solution with ethylene. The catalyst solution is prepared by dissolving 10 mg of rac-(ferroceno[2,3]inden-1-yl)dimethylsilylene(tetramethylcyclopentadienyl)zirconium dichloride in 4.7 ml of toluene and mixing with 10.8 g of 10% strength MAO. The pressure in the reactor is kept at a constant 8 bar during the entire polymerization time by metering in further amounts of monomer. The stirrer speed is 700 revolutions per minute, the polymerization time is 2 hours.

32 g of polyethylene having a molecular weight M$_w$=672,000 g/mol and a polydispersity M$_w$/M$_n$=6.9 were obtained.

EXAMPLE 4

A 2 l stirred reactor is made inert under nitrogen, 2.3 g of 10% strength MAO and 1 dm$^3$ of n-hexane are then metered in and the mixture is stirred for 15 minutes. After degassing the suspension medium and heating the reactor to the reaction temperature of 70° C., the polymerization is started by injecting the catalyst solution with an ethylene/propylene mixture containing 11.3 mol % of propylene. The catalyst solution is prepared by dissolving 10 mg of rac-(ferroceno[2,3]inden-1-yl)dimethylsilylene(cyclopentadienyl)zirconium dichloride in 0.9 ml of toluene and mixing with 2.2 g of 10% strength MAO.

The pressure in the reactor is kept at a constant 2.5 bar during the entire polymerization time by metering in further amounts of the gas mixture. The stirrer speed is 700 revolutions per minute, the polymerization time is 1 hour.

33.2 g of ethylene/propylene copolymer having a molecular weight M$_w$=30,000 g/mol and a polydispersity M$_w$/M$_n$=3.7 were obtained. The propylene content is 1.8 mol %.

EXAMPLE 5

The procedure is similar to that of Example 2. The intially charged propylene is stirred with 10.8 g of 10% strength MAO. The catalyst solution is prepared by dissolving 10 mg of rac-(ferroceno[2,3]inden-1-yl)dimethylsilylene(tetramethylcyclopentadienyl)zirconium dichloride in 4.7 ml of toluene and mixing with 10.8 g of 10% strength MAO.

4.0 g of an ethylene/propylene copolymer having a molecular weight M$_w$=41,000 g/mol and a polydispersity M$_w$/M$_n$=8.0 were obtained. The propylene content is 14.3 mol %.

EXAMPLE 6

The procedure is similar to that of Example 3. The hexane is stirred with 3.9 g of 30% strength MAO. The catalyst solution is prepared by dissolving 5 mg of bis(ferroceno[2,3]inden-1-yl)dimethylsilylenezirconium dichloride in 10.4 ml of toluene and mixing with 3.9 g of 10% strength MAO.

4.3 g of polyethylene having a molecular weight M$_w$=761,000 g/mol and a polydispersity M$_w$/M$_n$=16.7 were obtained.

EXAMPLE 7

The procedure is similar to that of Example 4. The hexane initially charged is stirred with 10.8 g of 10% strength MAO. The catalyst solution is prepared by dissolving 10 mg of rac-(ferroceno[2,3]inden-1-yl)dimethylsilylene(tetramethylcyclcopentadienyl)zirconium dichloride in 4.7 ml of toluene and mixing with 10.8 g of 10% strength MAO.

34.6 g of an ethylene/propylene copolymer having a molecular weight $M_w$=821,000 g/mol and a polydispersity $M_w/M_n$=6.3 were obtained. The propylene content is 1.7 mol %.

EXAMPLE 8

The procedure is similar to that of Example 1. The propylene initially charged is stirred with 10.1 g of 10% strength MAO. The catalyst solution is prepared by dissolving 10 mg of rac-(ferroceno[2,3]inden-1-yl)dimethylsilylene(cyclopentadienyl)zirconium dichloride in 5.9 ml of toluene and mixing with 10.1 g of 10% strength MAO. The polymerization temperature is 20° C.

11.8 g of polypropylene having a molecular weight $M_w$=10,000 g/mol and a polydispersity $M_w/M_n$=3.0 were obtained.

EXAMPLE 9

The procedure is similar to that of Example 1. The propylene initially charged is stirred with 3.1 g of 30% strength MAO. The catalyst solution is prepared by dissolving 10 mg of rac-(ferroceno[2,3]inden-1-yl)dimethylsilylene(2-methylinden-1-yl)hafnium dichloride in 5.9 ml of toluene and mixing with 3.1 g of 10% strength MAO.

16.3 g of polypropylene having a molecular weight $M_w$=38,000 g/mol and a polydispersity $M_w/M_n$=3.8 were obtained.

EXAMPLE 10

The procedure is similar to that of Example 4. 1 dm³ of toluene is initially charged in place of hexane and is stirred with 1.1 g of 10% strength MAO. The catalyst solution is prepared by dissolving 1 mg of rac(ferroceno[2,3]inden-1-yl)dimethylsilylene(cyclopentadienyl)zirconium dichloride in 0.45 ml of toluene and mixing with 1.1 g of 10% strength MAO.

39.3 g of an ethylene/propylene copolymer having a molecular weight $M_w$=107,000 g/mol and a polydispersity $M_w/M_n$=3.5 were obtained. The propylene content is 1.7 mol %.

EXAMPLE 11

The procedure is similar to that of Example 3. The hexane initially charged is stirred with 7.5 g of 10% strength MAO. The catalyst solution is prepared by dissolving 10 mg of bis(9-ferrocenylfluorenyl)titanium dichloride in 1.3 ml of toluene and mixing with 7.5 g of 10% strength MAO.

3.0 g of polyethylene having a molecular weight $M_w$=1,196,000 g/mol and a polydispersity $M_w/M_n$=24.2 were obtained.

EXAMPLE 12

The procedure is similar to that of Example 4. The hexane initially charged is stirred with 3.4 g of 30% strength MAO. The catalyst solution is prepared by dissolving 10 mg of rac-(ferroceno[2,3]inden-1-yl)dimethylsilylene(fluoren-9-yl)zirconium dichloride in 5.7 ml of toluene and mixing with 3.3 g of 30% strength MAO. The reactor pressure is 2.4 bar.

5.5 g of an ethylene/propylene copolymer having a molecular weight $M_w$=205,000 g/mol and a polydispersity $M_w/M_n$=8.9 were obtained. The propylene content is 2.1 mol %.

EXAMPLE 13

The procedure is similar to that of Example 4. The hexane initially charged is stirred with 3.9 g of 30% strength MAO. The catalyst solution is prepared by dissolving 10 mg of rac-(ferroceno[2,3]inden-1-yl)dimethylsilylene(t-butylamido)zirconium dichloride in 5 ml of toluene and mixing with 3.9 g of 30% strength MAO. The reactor pressure is 2.4 bar.

2.2 g of an ethylene/propylene copolymer having a molecular weight $M_w$=176,000 g/mol and a polydispersity $M_w/M_n$=5.3 were obtained. The propylene content is 1.2 mol %.

EXAMPLE 14

The procedure is similar to that of Example 4. The hexane initially charged is stirred with 2.9 g of 30% strength MAO. The catalyst solution is prepared by dissolving 10 mg of rac-(4-ferrocenylferroceno[2,3]cyclopentadienyl)dimethylsilylene(tetramethylcyclopentadienyl)zirconium dichloride in 7.5 ml of toluene and mixing with 2.9 g of 30% strength MAO. The reactor pressure is 2.4 bar. 14.8 g of an ethylene/propylene copolymer having a molecular weight $M_w$=146,000 g/mol and a polydispersity $M_w/M_n$=4.6 were obtained. The propylene content is 0.8 mol %.

EXAMPLE 15

The procedure is similar to that of Example 4. The hexane initially charged is stirred with 2.1 g of 30% strength MAO. The catalyst solution is prepared by dissolving 10 mg of bis(4-ferrocenylferroceno[2,3]cyclopentadienyl)dimethylsilylenezirconium dichloride in 9.6 ml of toluene and mixing with 2.1 g of 30% strength MAO. The reactor pressure is 2.4 bar.

2.4 g of an ethylene/propylene copolymer having a molecular weight $M_w$=187,000 g/mol and a polydispersity $M_w/M_n$=4.1 were obtained. The propylene content is 0.4 mol %.

EXAMPLE 16

A 2 l stirred reactor is made inert under nitrogen, 3.9 g of 30% strength MAO, 0.5 dm³ of n-hexane and 0.5 dm³ of cyclopentene are then metered in and the mixture is stirred for 15 minutes. After degassing the monomer solution and heating the reactor to the reaction temperature of 70° C., the polymerization is started by injecting the catalyst solution with ethylene. The catalyst solution is prepared by dissolving 10 mg of rac(ferroceno[2,3]inden-1-yl)dimethylsilylene(cyclopentadienyl)zirconium dichloride in 5.1 ml of toluene and mixing with 4.0 g of 30% strength MAO.

The pressure in the reactor is kept at a constant 1 bar during the entire polymerization time by metering in further amounts of monomer. The stirrer speed is 700 revolutions per minute, the polymerization time is 2 hours.

85.4 g of ethylene/cyclopentene copolymer having a molecular weight $M_w$=16,000 g/mol and a polydispersity $M_w/M_n$=2.4 were obtained. The cyclopentene content is 3.2 mol %.

EXAMPLE 17

A 2 l stirred reactor is made inert under nitrogen, 3.9 g of 30% strength MAO and 0.5 dm$^3$ of cyclopentene are then metered in and the mixture is stirred for 15 minutes. After degassing the monomer and heating the reactor to the reaction temperature of 70° C., the polymerization is started by injecting the catalyst solution with nitrogen. The catalyst solution is prepared by dissolving 10 mg of rac-(ferroceno[2,3]inden-1-yl)dimethylsilylene(cyclopentadienyl)zirconium dichloride in 5.2 ml of toluene and mixing with 4.0 g of 30% strength MAO. The stirrer speed is 700 revolutions per minute, the polymerization time is 2 hours.

11.8 g of polycyclopentene of wax-like consistency were obtained.

EXAMPLE 18

The procedure is similar to that of Example 16. 200 ml of cyclopentene are dissolved in 800 ml of hexane and stirred with 5.7 g of 30% strength MAO. 14.5 mg of rac-(ferroceno[2,3]inden-1-yl)dimethylsilylene(cyclopentadienyl)zirconium dichloride are then dissolved in 8.5 ml of toluene and mixed with 5.7 g of 30% strength MAO. The ethylene pressure is 2 bar, the polymerization temperature is 30° C. 18.3 g of ethylene/cyclopentene copolymer having a molecular weight $M_w=771{,}000$ g/mol and a polydispersity $M_w/M_n=3.9$ were obtained. The cyclopentene content is 0.5 mol %.

EXAMPLE 19

A 2 l stirred reactor is made inert under nitrogen, 3.9 g of 30% strength MAO and 0.5 dm$^3$ of cyclopentene are then metered in and the mixture is stirred for 15 minutes. After degassing the monomer and heating the reactor to the reaction temperature of 50° C., the polymerization is started by injecting the catalyst solution with ethylene. The catalyst solution is prepared by dissolving 10 mg of rac-(ferroceno[2,3]inden-1-yl)dimethylsilylene(cyclopentadienyl)zirconium dichloride in 4.5 ml of toluene and mixing with 4.0 g of 30% strength MAO.

The pressure in the reactor is kept at a constant 1 bar during the entire polymerization time by metering in further amounts of monomer. The stirrer speed is 700 revolutions per minute, the polymerization time is 0.5 hours.

97.4 g of ethylene/cyclopentene copolymer having a molecular weight $M_w=29{,}000$ g/mol and a polydispersity $M_w/M_n=2.4$ were obtained. The cyclopentene content is 3.4 mol %.

EXAMPLE 20

The procedure is similar to that of Example 19. 4.0 g of 30% strength MAO are dissolved in cyclopentene. The catalyst solution consists of 10 mg of rac-(ferroceno[2,3]inden-1-yl)dimethylsilylene(cyclopentadienyl)zirconium dichloride, 4.5 ml of toluene and 3.9 g of 30% strength MAO. The polymerization time is 2 hours. 60.8 g of ethylene/cyclopentene copolymer having a molecular weight $M_w=3000$ g/mol and a polydispersity $M_w/M_n=2.0$ were obtained. The cyclopentene content is 35 mol %.

EXAMPLE 21

The procedure is similar to that of Example 19. 1 g of 10% strength MAO is dissolved in cyclopentene. The catalyst solution consists of 2 mg of rac-(ferroceno[2,3]inden-1-yl)dimethylsilylene(cyclopentadienyl)zirconium dichloride, 0.9 ml of toluene and 1 g of 10% strength MAO. The polymerization time is 2 hours. 6.1 g of ethylene/cyclopentene copolymer having a molecular weight $M_w=32{,}000$ g/mol and a polydispersity $M_w/M_n=4.0$ were obtained. The cyclopentene content is 2.6 mol %.

EXAMPLE 22

The procedure is similar to that of Example 19. 5 g of 10% strength MAO are dissolved in cyclopentene. The catalyst solution consists of 2 mg of rac-(ferroceno[2,3]inden-1-yl)dimethylsilylene(cyclopentadienyl)zirconium dichloride, 0.9 ml of toluene and 4.9 g of 10% strength MAO. The polymerization time is 2 hours. 81.9 g of ethylene/cyclopentene copolymer having a molecular weight $M_w=37{,}000$ g/mol and a polydispersity $M_w/M_n=2.3$ were obtained. The cyclopentene content is 2.6 mol %.

EXAMPLE 23

The procedure is similar to that of Example 1. The propylene initially charged is stirred with 23.4 g of 30% strength MAO. The catalyst solution is prepared by dissolving 92 mg of o,o'-bis(ferroceno[2,3]inden-1-yl)biphenylenezirconium dichloride in 40 ml of toluene and mixing with 23.4 g of 30% strength MAO. The polymerization temperature is 50° C.

75.2 g of polypropylene having a molecular weight $M_w=37{,}000$ g/mol and a polydispersity $M_w/M_n=3.4$ were obtained.

What we claim is:

1. Metallocene of the formula I

(I)

where

M is a metal selected from the group consisting of Ti, Zr, Hf, V, Nb, Ta or an element selected from the group of the lanthanides, $X_1$ and $X_2$ are identical or different and are each a $C_1$–$C_{10}$-alkyl group, a $C_1$–$C_{10}$-alkoxy group, a $C_6$–$C_{10}$-aryl group, a $C_6$–$C_{10}$-aryloxy group, a $C_2$–$C_{10}$-alkenyl group, a $C_7$–$C_{20}$-arylalkyl group, a $C_7$–$C_{20}$-alkylaryl group, a $C_8$–$C_{20}$-arylalkenyl group, hydrogen or a halogen atom, $L_1$ and $L_2$ a) are identical or different and are each an unsubstituted, monosubstituted or polysubstituted monocyclic or polycyclic hydrocarbon radical having at least one cyclopentadienyl unit, which hydrocarbon radical forms a sandwich structure with M, where $L_1$ and/or $L_2$ is substituted by and/or condensed with one or more substituted or unsubstituted ferrocene or ruthenocene radicals, where the substituents of the hydrocarbon radical, of the ferrocene radical and of ruthenocene radical have the same meanings as $X_1$ and $X_2$ or are a ferrocene or ruthenocene radical, or b) $L_1$ is an unsubstituted, monosubstituted or polysubstituted monocyclic or polycyclic hydrocarbon radical having at least one cyclopentadienyl unit, which hydrocarbon radical forms a sandwich structure with M and which is substituted by and/or condensed with one or more substituted or unsubstituted ferrocene or ruthenocene radicals, where the substituents of the hydrocarbon radical, of the ferrocene radical and of ruthenocene radical have the same meanings as $X_1$ and $X_2$ or are a ferrocene or ruthenocene radical and $L_2$ is an amido, phosphido or arsenido radical of the formula

where D is nitrogen, phosphorus or arsenic and E has the meaning of $X_1$ and $X_2$, $R_1$ is carbon, silicon, germanium or tin, or the entire bridge $A(R_1)_nB$ is a biphenylene radical which is unsubstituted or substituted by A and/or B, A and B have the meanings of $X_1$ and $X_2$, and n is an integer from 0 to 4, where in the case n=0, the free valencies of $L_1$ and $L_2$ are substituted by a radical $X_1$ or $X_2$, with the proviso that in the case of $L_2$ being an amido, phosphido or arsenido radical, n is not equal to zero.

2. Metallocenes according to claim 1, wherein $L_1$ is ferroceno[2,3]inden-1-yl, ferroceno[2,3]-cyclopentadien-1-yl, 4-ferrocenylferroceno[2,3]cyclopentadien-1-yl, or 9-ferrocenylfluorenyl, and $L_2$ has the same meanings or is cyclopentadienyl, tetramethylcyclopentadienyl, inden-1-yl, 2-methylinden-1-yl, or fluorenyl.

3. Metallocenes according to claim 1, selected from the group consisting of bis(ferroceno[2,3]inden-1-yl)dimethylsilylenezirconium dichloride, rac-(ferroceno[2,3]inden-1-yl)dimethylsilylene(tetramethylcyclopentadienyl)zirconium dichloride, rac-(ferroceno[2,3]inden-1-yl)dimethylsilylene(cyclopentadienyl)zirconium dichloride, rac-(ferroceno[2,3]inden-1-yl)dimethylsilylene(2-methylinden-1-yl)hafnium dichloride, rac-(ferroceno[2,3]-inden-1-yl)dimethylsilylene-(fluoren- 9-yl)zirconium dichloride, rac-(ferroceno[2,3]inden-1-yl)dimethyl-silylene(t-butylamido)zirconium dichloride, rac-(4-ferrocenylferroceno[2,3]cyclopentadienyl)dimethylsilylene(tetramethylcyclopentadienyl)zirconium dichloride, bis(4-ferrocenylferroceno[2,3]cyclopentadienyl)dimethylsilylenezirconium dichloride, bis(9-ferrocenylfluorenyl)titanium dichloride and o,o'-bis-(ferroceno[2,3]inden-1-yl)biphenylenezirconium dichloride.

4. Process for preparing polyolefins by polymerization of olefins, which comprises contacting olefins with a polymerization catalyst, wherein metallocenes according to claim 1 are used as catalysts.

5. Process for preparing polyolefins by polymerization of olefins, which comprises contacting olefins with a polymerization catalyst, wherein metallocenes according to claim 1 are used as catalysts, and aluminoxanes are used as co-catalysts in addition to the metallocenes.

* * * * *